(12) United States Patent
Savidge

(10) Patent No.: US 6,209,387 B1
(45) Date of Patent: Apr. 3, 2001

(54) SYSTEM AND METHOD FOR DETERMINING THERMODYNAMIC PROPERTIES

(75) Inventor: Jeffrey L. Savidge, Algonquin, IL (US)

(73) Assignee: Gas Research Institute, Chicago, IL (US)

(*) Notice: Subject to any disclaimer, the term of this patent is extended or adjusted under 35 U.S.C. 154(b) by 0 days.

(21) Appl. No.: 09/342,383

(22) Filed: Jun. 29, 1999

Related U.S. Application Data

(63) Continuation-in-part of application No. 08/903,069, filed on Jul. 30, 1997, now Pat. No. 5,932,793, which is a continuation-in-part of application No. 08/903,314, filed on Jul. 30, 1997.

(51) Int. Cl.[7] .......................... G01N 29/02; G01N 09/00; G01F 1/86; G01L 9/08
(52) U.S. Cl. ................... 73/24.05; 73/23.29; 73/25.01; 73/589; 73/597
(58) Field of Search .................. 73/24.05, 23.2, 73/23.29, 25.01, 589, 597, 646, 861.28, 1 G

(56) References Cited

U.S. PATENT DOCUMENTS

| | | | |
|---|---|---|---|
| H465 | 5/1988 | Hill et al. ............................. 367/181 |
| 2,711,646 | 6/1955 | Mendousse .............................. 73/53 |
| 2,837,914 | 6/1958 | Caldwell ............................... 73/67.1 |
| 2,903,884 | 9/1959 | Kritz .................................... 73/32 |
| 2,926,522 | 3/1960 | Kritz .................................... 73/32 |
| 2,978,899 | * | 4/1961 | Kritz .................................... 73/24 |
| 3,017,607 | 1/1962 | Rubens et al. .......................... 340/5 |
| 3,028,749 | 4/1962 | Welkowitz ............................... 73/32 |
| 3,233,461 | * | 2/1966 | Heckl et al. ........................... 73/388 |
| 3,572,094 | * | 3/1971 | Banks ................................... 73/30 |
| 3,604,252 | 9/1971 | Beeken ................................... 73/69 |
| 3,710,615 | 1/1973 | Johnson et al. ....................... 73/61 R |
| 3,791,200 | 2/1974 | Hayre .................................. 73/67.1 |
| 3,911,726 | 10/1975 | Georgiev ............................... 73/32 A |
| 4,262,523 | 4/1981 | Stansfeld ................................ 73/30 |
| 4,320,659 | 3/1982 | Lynnworth et al. ..................... 73/589 |
| 4,325,255 | 4/1982 | Howard et al. ......................... 73/589 |
| 4,450,929 | * | 5/1984 | Marrs .................................. 181/146 |

(List continued on next page.)

OTHER PUBLICATIONS

A..F. Estrada–Alexanders et al.: Thermodynamic Properties of Gaseous Argon at Temperatures Between 110 and 450K and Densities up to 6.8 Mol•dm$^{-3}$ Determined from the Speed of Sound, *International Journal of Thermophysics*, vol. 17, No. 6, 1996, Apr. 1996.

(List continued on next page.)

*Primary Examiner*—Hezron Williams
*Assistant Examiner*—David J. Wiggins
(74) *Attorney, Agent, or Firm*—Pauley Petersen Kinne & Fejer

(57) ABSTRACT

Disclosed is a system and method for determining the thermodynamic properties and percentage of each component of a multi-component gas medium by using speed of sound in conjunction with other data. The present system comprises a computer system with means for obtaining the temperature, pressure, and speed of sound of a gas medium. The computer system operates according to operating logic stored in memory. According to the operating logic, measurements of the temperature, pressure, speed of sound and acoustic impedance are recorded in a gas pipe or other transport device to determine a convergent temperature range. Next a convergent series is extrapolated from the convergent temperature range and a convergent series calculation using isochoric convergence iterations is performed to obtain estimates of the thermo-physical properties of the gas medium. Thereafter, the percentage of the gas medium which comprises each known gas components is determined using state equations and the estimated thermo-physical properties.

12 Claims, 8 Drawing Sheets

U.S. PATENT DOCUMENTS

| | | | |
|---|---|---|---|
| 4,489,592 | | 12/1984 | Pacanowski et al. .................... 73/30 |
| 4,614,115 | | 9/1986 | Pelletier et al. ....................... 73/599 |
| 4,648,275 | | 3/1987 | Goodman ............................... 73/589 |
| 4,663,977 | | 5/1987 | Vander Heyden ............... 73/861.27 |
| 4,763,524 | | 8/1988 | Goodman ............................... 73/589 |
| 4,790,183 | | 12/1988 | Pfost et al. ......................... 73/290 V |
| 4,872,335 | | 10/1989 | Tsuruoka et al. ........................ 73/30 |
| 5,159,843 | | 11/1992 | Shakkottai et al. ................. 73/24.05 |
| 5,214,955 | * | 6/1993 | Yost et al. ............................ 73/24.05 |
| 5,285,675 | | 2/1994 | Colgate et al. ....................... 73/23.2 |
| 5,311,447 | | 5/1994 | Bonne ................................. 364/509 |
| 5,343,758 | | 9/1994 | Ingrain et al. ..................... 73/864.02 |
| 5,386,714 | * | 2/1995 | Dames ................................. 73/24.05 |
| 5,467,637 | * | 11/1995 | Hasegawa et al. ................. 73/24.01 |
| 5,526,675 | * | 6/1996 | Ratton .................................. 73/23.2 |
| 5,531,096 | * | 7/1996 | Castor .................................. 73/23.2 |
| 5,533,389 | * | 7/1996 | Kamen et al. ......................... 73/149 |
| 5,551,282 | * | 9/1996 | VanderHeyden et al. .......... 73/30.03 |
| 5,600,610 | | 2/1997 | Hill et al. ............................. 367/181 |
| 5,693,873 | | 12/1997 | Thuries et al. ...................... 73/23.28 |
| 5,932,793 | | 8/1999 | Dayton et al. ...................... 73/24.05 |

OTHER PUBLICATIONS

A..F. Estrada–Alexanders et al.: The Speed of Sound and Derived Thermodynamic Properties of Ethane at Temperatures between 220K and 450K and Pressures up to 10.5 MPa, *J. Chem. Thermodynamics*, 29, 991–1015, Jun. 1997.

J.P.M. Trusler: Physical Acoustics and Metrology of Fluids, *The Adam Hilger Series on Measurement Science and Technology*, 1–9, ISBN 0–7503–0113–9, Adam Hilger, IOP Publishing Ltd, England and New York, 1991.

J.P.M. Trusler et al.: The Speed of Sound and Derived Thermodynamic Properties of Mehane at Temperatures between 275K and 375K and Pressures up to 10 MPa, *J. Chem. Thermodynamics*, 24, 973–991, Feb. 1992.

A..F. Estrada–Alexanders et al.: Determination of Thermodynamic Properties from the Speed of Sound, *International Journal of Thermophysics*, vol. 16, No. 3, 663–673, Mar. 1995.

* cited by examiner

SYSTEM AND METHOD FOR DETERMINING THERMODYNAMIC PROPERTIES

CROSS-REFERENCE TO RELATED APPLICATIONS

This application is a continuation-in-part of, and claims priority to, commonly assigned U.S. patent application entitled "Apparatus and Method for Determining Thermophysical Properties Using an Isochoric Approach" filed on Jul. 30, 1997 and accorded Ser. No. 08/903,069 now U.S. Pat. No. 5,932,793. The subject matter of this document is also a continuation-in-part of, and claims priority to, co-pending and commonly assigned U.S. patent application entitled "Apparatus and Method for Determining Thermophysical Properties Using an Isobaric Approach" filed on Jul. 30, 1997, and accorded Ser. No. 08/903,314. The foregoing documents are incorporated herein by reference in their entirety.

STATEMENT REGARDING FEDERALLY SPONSORED RESEARCH OR DEVELOPMENT

Not Applicable.

TECHNICAL FIELD

This invention relates to the field of determining the proportional chemical make up of a multi-component gas, and more particularly, to determining the proportional makeup by measuring the thermo-physical properties of multi-component gasses using speed of sound data.

BACKGROUND OF THE INVENTION

Accurate thermodynamic properties of hydrocarbons are essential for analyzing processes related to liquification, transportation, processing and storage of gaseous fuels. Among the properties of interest are the compression factor, heat capacity, entropy, enthalpy and others. These properties must be known about various gas mediums which are made of a mixture of components. Such parameters are used in determining the precise makeup of storage vessels and processing equipment as well as a multitude of other applications.

These properties are generally calculated from an equation of state using so called look up tables for the particular gas medium. However, these lookup tables do not include parameters for gas mediums that are composed of a mixture of elements. Also, the accuracy of properties calculated from an equation of state depends upon the accuracy of the experimental data used in the fitting process.

The state-of-the-art technology used to measure the thermodynamic characteristics of multi-component gas mediums include the use a gas chromatograph to determine the precise chemical makeup of the medium as known to those skilled in the art. Such equipment is quite expensive to produce, thereby raising the cost of determining the thermodynamic characteristics of a multi-component gas medium.

SUMMARY OF THE INVENTION

The present invention entails a system and method for determining the thermodynamic properties of a gas comprised of a mixture of elements by using speed of sound in conjunction with other data, where the precise components are known, but their proportionality is unknown. For purposes of this discussion, a gas that is made up of several elements is termed a multi-component gas. In the preferred embodiment, the density of a multi-component gas medium is ascertained by determining the acoustic impedance of, and the speed of sound though the gas medium and recording the measurements of these parameters.

The acoustic impedance of the gas medium is determined from the voltage loss across the transducer at maximum energy transfer to the gas medium at the transducer resonant frequency.

In the instant invention, the speed of sound through a particular gas medium is determined by timing the propagation of a sonic pulse sent through the gas medium. The sonic pulse is created by an ultrasonic transducer. The return pulse is detected by the transducer and sent back to the transducer interface. The transducer interface is connected to a data bus where a central processing unit will access the pulse timing information and calculate the actual speed of sound.

From the acoustic impedance and the speed of sound, the density of the multi-component gas is determined. Also, the temperature and pressure of the gas medium are measured. The system repeatedly measures these parameters and stores them in memory.

Next, the system examines the data gathered for a convergent temperature range from which a convergent series may be extrapolated. Once this range is found, the values of the measured parameters are extrapolated into a convergence series from which the thermo-physical properties of the multi-component gas are calculated. Thereafter, the thermo-physical properties calculated are employed to determine the precise makeup of the multi-component gas as a percentage of each component.

The present invention also provides for a method for determining the thermodynamic properties of a multi-component gas medium. The method comprises the steps of measuring the pressure, speed of sound, and acoustic impedance of the gas medium for particular temperatures and storing the measurements in memory. Thereafter, a convergent temperature range is identified from the stored measurements.

Once the convergent temperature range is identified, the step of calculating the thermodynamic properties of the gas medium is undertaken by performing several iterations of a convergent series extrapolated from the convergent temperature range. Finally, the step of determining the percentage of a plurality of gas components making up the gas medium is performed.

Other features and advantages of the present invention will become apparent to one with skill in the art upon examination of the following drawings and detailed description. It is intended that all such additional features and advantages be included herein within the scope of the present invention, as defined by the claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. In the drawings, like reference numerals designate corresponding parts throughout the several views.

DETAILED DESCRIPTION OF THE PREFERRED EMBODIMENT

Figure 1:
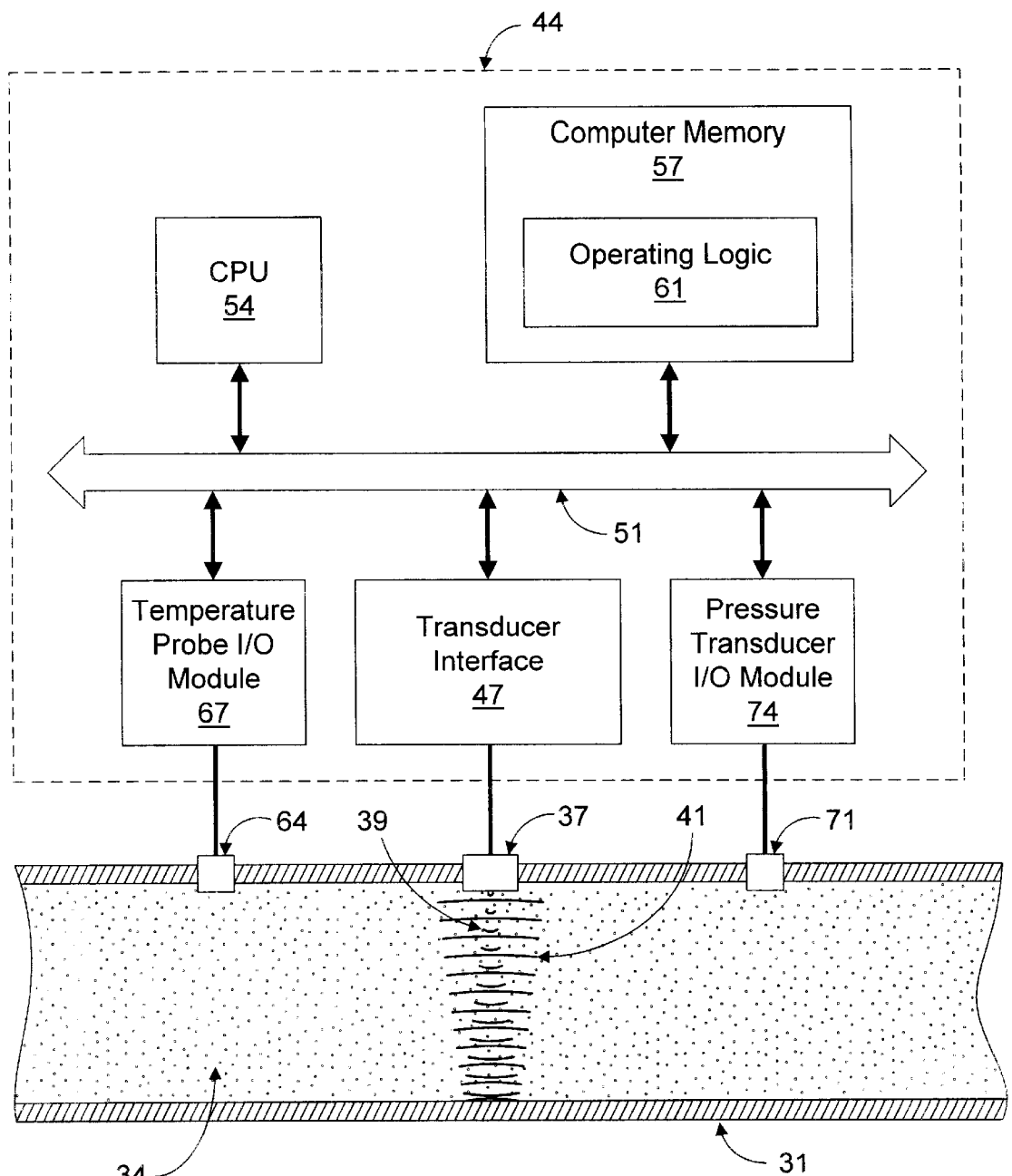
FIG. 1 is a block diagram of the system according to the present invention.

Turning to FIG. 1, an overview of the system according to the first embodiment is shown in which pipe 31 is filled with a gas medium 34. For the purposes of this disclosure, "medium" is defined as the gas 34 tested and is referred to as the "medium" 34. It should be noted that the medium 34 referred to herein is a multi-component gas, however, such gasses could also be comprised of a single element. The medium 34 may be, for example, a multi-component gas in which the actual chemical components are known, but the proportionality of the components is unknown. On one side of the pipe 31 is affixed the transducer 37 in such an orientation so that that it may produce a sonic pulse 39 which is sent into the pipe 31. The transducer 37 may be of the type described in U.S. Pat. No. 5,600,610 filed on Jan. 31, 1995, entitled "Electrostatic Transducer and Method for Manufacturing Same", the entire text of which is incorporated herein by reference.

The transducer 37 is in electrical communication with computer system 44 via transducer interface 47. The transducer interface 47 is electrically coupled to a common data bus 51 in computer system 44. Also connected to the data bus 51 are the central processor unit 54 and the computer memory 57. Stored within the computer memory 57 is the operating logic 61.

Also, a temperature sensor 64 is affixed to the pipe 31 and is electrically coupled with the data bus 51 via the temperature sensor input/output module 67. The temperature sensor 64 makes temperature data of the medium 34 available on the data bus 51 through the temperature sensor input/output module 67. Note that the temperature sensor 64 may be placed at any position within the pipe 31 beyond the position shown. Also, multiple temperature sensors 64 may be employed to determine the temperature at multiple points in the pipe 31.

Finally, a pressure transducer 71 is affixed to the pipe 31 and is electrically coupled to the data bus 51 via the pressure transducer input/output module 74. The pressure transducer 71 makes pressure data of the medium 34 available on the data bus 51 through the pressure transducer input/output module 74. Also, similar to the temperature sensor 64 above, the pressure transducer 71 can be positioned at any point within the pipe 31, and multiple pressure transducers 71 may be employed as well.

According to the general operation of the above described system, the computer system 44, operating pursuant to the software 61 will cause the transducer interface 47 to send an excitation signal to the transducer 37. The transducer 37 will then create a sonic pulse 39 which is directed into the medium 34 held by the pipe 31. The sonic pulse 41 will travel across the medium 34 striking the wall of the pipe 31 opposite the transducer 37. A reflected sonic pulse 41 will then reflect off of the opposing wall and propagate back toward the transducer 37. The transducer 37 detects the reflected sonic pulse 41 and sends a signal to the transducer interface 47. This signal triggers action on the part of the computer system 44 according to the operating logic 61. Temperature measurements from the temperature sensor 64 and pressure measurements from the pressure transducer 74 are also read and stored by the computer system 44 according to the operating logic 61.

Figure 2:
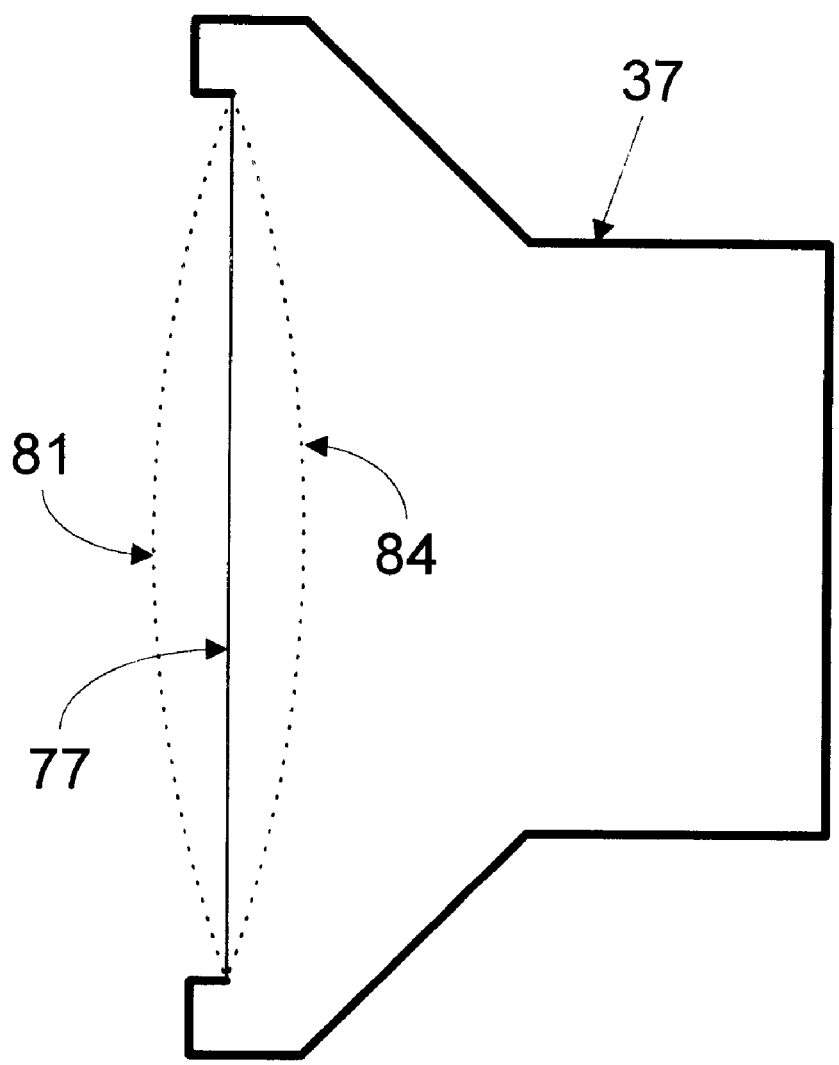
FIG. 2 is a drawing of a cross-sectional view of the transducer of FIG. 1.

Turning to FIG. 2, shown is a basic transducer 37 having a membrane 77. The membrane 77 is caused to move back and forth in response to an excitation signal between the extended position 81 and the retracted position 84. The extended and retracted positions are inherent in the design of the transducer 37 as known to one skilled in the art. To explain further, when extended 81 or retracted 84, the membrane 77 has a natural tendency to rebound. The membrane 77 ultimately oscillates back and forth until coming to rest in the middle. In this way, the membrane 77 has a natural frequency of oscillation that depends on both the construction of the membrane 77 itself and the nature and properties of the medium in which it is positioned.

Figure 3:
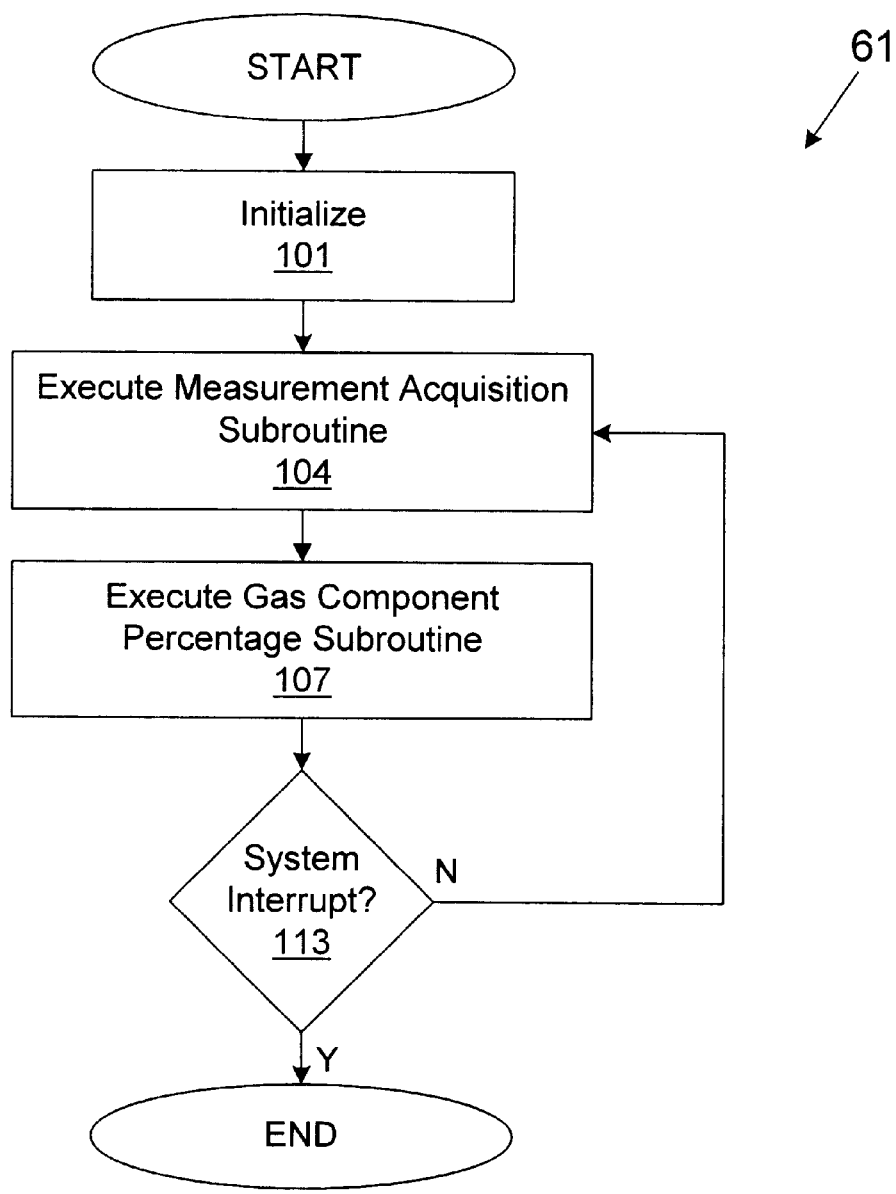
FIG. 3 is a flow chart illustrating the main operating logic stored in the memory of FIG. 1.

Turning then to FIG. 3, a flow chart which illustrates the operating logic 61 (FIG. 1) is shown. In block 101 the system is initialized while the system is brought on line. This entails executing various startup programs, etc. to ready the computer system 44 (FIG. 1) to begin operation. In particular, the temperature sensor(s) 64, pressure transducer (s) 71, and the sonic transducer 37 are tested for proper function. Also, a number of default parameters are loaded into the memory 57 for use by the operating logic 61. These default parameters may be stored on a permanent memory storage device such as a hard drive disk (not shown) and may be set independently by the user.

Thereafter, in block 104, a subroutine is executed in which measurements of the temperature, pressure, speed of sound, and the acoustic impedance of the medium 34 (FIG. 1) are continually taken and stored in memory 57 (FIG. 1). In block 107, a gas component determination subroutine is executed in which a range of temperature values and corresponding measurements used in executing an isochoric convergence series are estimated based on the actual measurements obtained. Also, thermo-physical parameters of the medium 34 (FIG. 1) are calculated using the estimated isochoric convergence series. Finally, the percentage of each gas component of the medium 34 is determined by applying the thermo-physical parameters and other known information to predetermined state diagrams. Thereafter, the operating logic 61 progresses to block 113 in which it is determined if the system is interrupted due to an external termination input, fault condition, or other condition. If an interrupt is detected, then the operating logic 61 ceases operation. If not, then the operating logic 61 reverts back to block 104. In this manner, the operating logic 61 continually calculates the percentage of the components which make up the medium 34.

Figure 4:
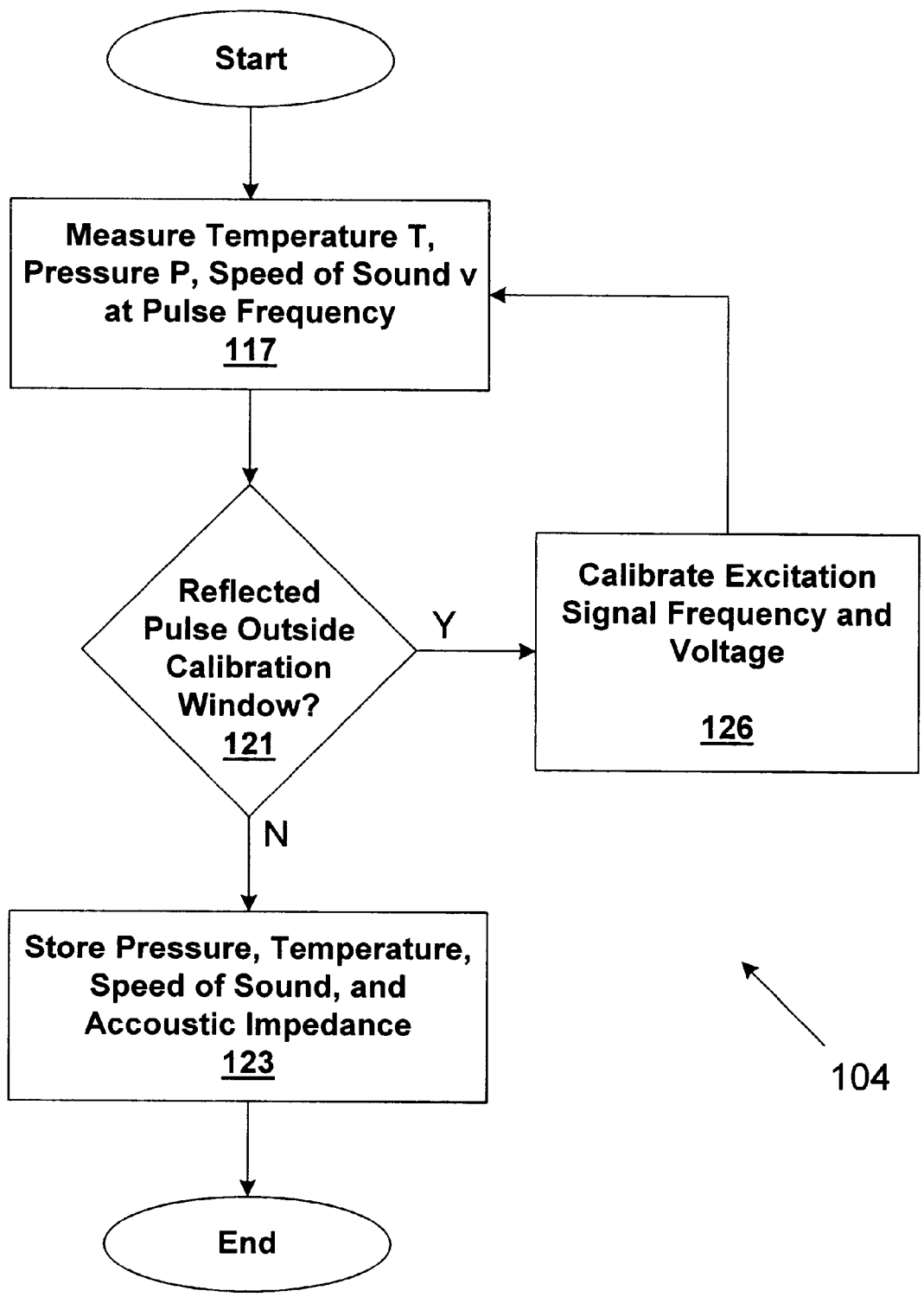
FIG. 4 is a flow chart illustrating the operating logic employed in the acquisition of physical measurements of FIG. 3.

Referring next to FIG. 4, shown is a flow diagram of the subroutine of block 104 (FIG. 3) in which physical measurements are taken according to the preferred embodiment. Beginning with block 117, the temperature T, pressure P, and the speed of sound v of the medium 34 (FIG. 1) are measured using the temperature sensor 64 (FIG. 1), pressure transducer 71 (FIG. 1), and the sonic transducer 37 (FIG. 1). The speed of sound is preferably determined using a "time of flight" method which is known in the art. This method involves sending a sonic pulse 39 (FIG. 1) into the medium 34 across a known distance where it reflects off of a surface. A reflected sonic pulse 41 (FIG. 1) travels back over the same distance to the sonic transducer 37. The speed of sound is then determined by dividing the distance traveled by the elapsed time between the sending of the sonic pulse 39 and receiving the reflected sonic pulse 41 as is known by those skilled in the art and will not be discussed in further detail. Initially, the frequency and voltage magnitude of the excitation signal which generates the sonic pulse 39 in the sonic transducer 37 is determined from default values read into the computer memory 57 during initialization of the computer system 44.

The subroutine operating logic 104 then progresses to block 121 in which the reflected sonic pulse 41 is examined to see if maximum power transfer is being achieved for accurate measurement of the acoustic impedance using the sonic transducer 37. This warrants further explanation.

Turning back to FIG. 2, recall that the transducer 37 has a membrane 77 that oscillates between the extended position 81 and the retracted position 84 in response to an excitation signal sent from the computer system 44 (FIG. 1) through the transducer interface 47 (FIG. 1). The membrane 77 oscillates at a natural frequency which is variable depending upon the physical circumstances of the medium 34 (FIG. 1) in which the transducer 37 is situated as well as the physical construction of the transducer 37 itself. Due to this fact, the sonic energy imparted into the medium 34 is greatest when the frequency of the excitation signal matches the resonant frequency of the transducer membrane 77.

To explain further, if the frequency of the excitation signal does not match the resonant frequency of the membrane 77, then the natural tendency of the membrane 77 to oscillate fights the force against the membrane generated by the excitation signal. If the frequency of the excitation signal matches the resonant frequency, then the natural tendency of the membrane 77 to oscillate compliments the force generated by the excitation signal resulting in greater extension of the membrane 77, and a sonic pulse 39 of greater magnitude. These principles are discussed in a co-pending continuing application Ser. No. 08/833,805, entitled "Scan Assembly and Method for Calibrating the Width of an Input Pulse to an Ultrasonic Transducer of the Scan Assembly" filed on Apr. 9, 1997, the entire text and drawings of which are incorporated herein by reference.

In addition, if the excitation signal frequency equals the resonant frequency of the membrane 77 in the particular medium 34, then the magnitude of the sonic pulse 39 is at a maximum when the voltage of the excitation signal is of sufficient magnitude to achieve full extension of the membrane 77 into the extended and retracted positions 81 and 84. Thus, when the frequency of the excitation signal equals the resonant frequency of the membrane 77 in the medium 34, and, when the voltage of the excitation frequency is of the magnitude to achieve fall extension of the membrane 77, maximum power transfer is imparted into the medium 34.

Referring once again to FIG. 4, it is observed that in physical terms, the acoustic impedance of the medium 34 (FIG. 1) is the mechanical force that must be overcome by the membrane 77 (FIG. 2) in order to achieve the extended position. Thus, it is further observed that at maximum power transfer, the acoustic impedance of the medium 34 is proportional to the magnitude of the voltage of the excitation signal. The actual value of the acoustic impedance in relation to the particular voltage of the excitation signal may be determined by external experimentation with the transducer in a controlled setting.

With this in mind, attention is directed to block 121 in which the magnitude of the reflected sonic pulse 41 is examined to ascertain whether it falls within the predetermined calibration window. The calibration window is generally expressed as a percentage of the strength of the reflected sonic pulse 41 which results from a calibrated excitation signal. For example, if the calibration window is set at ten percent of the signal strength of the reflected sonic pulse 41 resulting from a calibrated excitation signal, then the magnitude of the reflected sonic pulse 41 is outside the calibration window when its magnitude dips to below ten percent of this value. Initial values for the calibration window and the strength of a reflected sonic pulse 41 resulting from a calibrated excitation signal are obtained from permanent memory storage and place in the computer memory 57 during system initialization in block 101 (FIG. 3).

If it is determined that the magnitude of the reflected sonic pulse 41 is within the calibration window in block 121, the subroutine operating logic 104 progresses to block 123. In block 123 the measurements of the pressure, temperature, and speed of sound are stored in the memory 57 (FIG. 1). Also, the acoustic impedance which was determined from the voltage of the excitation signal is stored as well. Once the measurements are stored in memory 57, the subroutine 104 ends.

If, on the other hand, in block 121 it is determined that the magnitude of the reflected sonic pulse 41 is not within the calibration window, the subroutine operating logic 104 moves to block 126 where the frequency and the voltage of the excitation signal are calibrated to ensure maximum power transfer. This calibration is done to ensure that the acoustic impedance is measured accurately as it is proportional to the excitation signal voltage at maximum power transfer. Once the calibration is finished in block 126, the logic 104 reverts back to block 117.

Note that the precise percentage for the calibration window is chosen to be small enough so that the value for the acoustic impedance is accurate. However, it should be kept in mind that too small a calibration window would cause constant calibration and may disrupt the operation of the system. Consequently, there is a trade-off between accuracy and operability which one skilled in the art is to balance according to the specific application.

Figure 5:
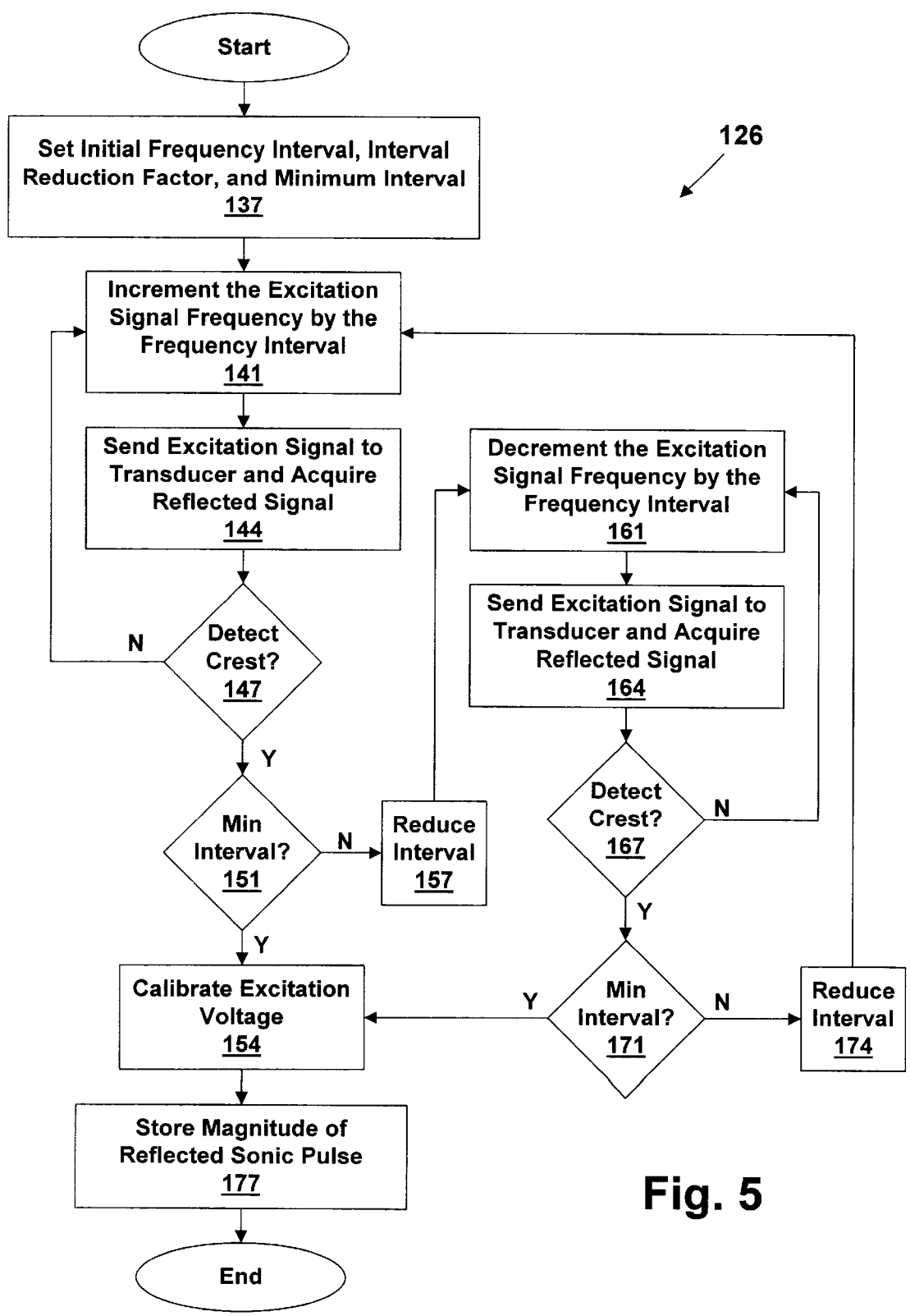
FIG. 5 is a flow chart illustrating the operating logic employed in the calibration of the excitation signal of FIG. 4.

Turning next to FIG. 5, a flow chart is shown which further illustrates the operating logic performed in calibrating the excitation signal frequency and voltage in block 126 (FIG. 4). Essentially, this subroutine increments the excitation frequency by a predetermined interval until a peak in the magnitude of the reflected sonic pulse 39 is detected. Next, the subroutine reverses direction and decrements the excitation frequency by a reduced interval until the peak in the magnitude is detected once again. The subroutine goes back and forth in this way reducing the interval each time until the actual frequency at which the reflected sonic pulse 39 is maximized. The voltage of the excitation signal is then calibrated, and, then the frequency and voltage are stored for use in acquiring speed of sound and acoustic impedance measurements.

Beginning then, with block 137, several predetermined variables are set including an initial frequency interval, an interval reduction factor, a minimum interval, and the excitation signal voltage. Next, in block 141, the frequency of the excitation signal is incremented by the predetermined frequency interval. In block 144, the excitation signal with the new frequency is transmitted to the transducer 37 (FIG. 1) which transmits the sonic pulse 39 and senses the reflected sonic pulse 41.

Next in block 147, the magnitude of the reflected sonic pulse 41 is compared to the magnitude of the previous reflected sonic pulse 41. If this magnitude is greater than magnitude of the last reflected sonic pulse 41 received, then the calibration operating logic 126 progresses back to block 141. If the magnitude is less, then the calibration operating logic 126 progresses to block 151. Block 147 determines whether the incremented frequency of the excitation pulse is moving away from or toward the frequency of maximum power transfer by examining whether the change in the magnitude of the excitation pulse at the incremented frequency is negative or positive as compared to the previous magnitude measured. If negative, then the incremented frequency is moving down the slope away from the frequency of maximum power transfer. If positive, then the incremented frequency is moving up the slope toward the frequency of maximum power transfer. Continued increments will eventually result in a negative value as the peak frequency is eventually is passed.

If a negative change in the magnitude of the reflected sonic pulse 39 is detected in block 147, the calibration operating logic 126 progresses to block 151 where it is determined if the intervals by which the excitation signal frequency is incremented or decremented are equal to or less than the predetermined minimum interval of block 137. If so, then the calibration operating logic 126 progresses to block 154. If not, then the operating logic progresses to block 157 where the interval is reduced by the predetermined interval reduction factor. In the preferred embodiment, the interval reduction is by a factor of 2.

After the interval is reduced in block 157, the calibration operating logic 126 progresses to block 161 where the excitation signal frequency is reduced by the frequency interval. Next, in block 164 the excitation signal is transmitted to the transducer 37 (FIG. 1) at the reduced frequency and the magnitude of the resulting reflected sonic pulse 41 is acquired. Then, in block 167, the magnitude of the reflected sonic pulse 41 is compared with the magnitude of the previous reflected sonic pulse 41 to detect whether the frequency of maximum power transfer has been passed. If the magnitude of the new reflected sonic pulse 41 is less, then the peak has been passed and the calibration operating logic 126 progresses to block 171. If it is greater, then the peak has not been passed and the calibration operating logic 126 progresses to back to block 161.

In block 171, the frequency interval is compared with the predetermined minimum interval as in block 151. If the frequency interval is less than or equal to the predetermined minimum interval, then the calibration operating logic 126 progresses to block 154. If it is greater than the minimum interval, then the calibration operating logic 126 progresses to block 174 where the frequency interval is reduced once again by the predetermined interval reduction factor. From block 174, the calibration operating logic 126 progresses to block 141 where the process is repeated.

If the calibration operating logic 126 progresses to block 154 from either block 151 or block 171, then the excitation signal frequency in which maximum power transfer has been achieved. In actuality, this frequency is an approximation where the tolerance is within the predetermined minimum interval as discussed above. In block 154, the magnitude of the excitation signal frequency voltage is calibrated for maximum extension of the transducer membrane 77 (FIG. 2).

Finally, in block 177, the voltage and frequency of the sonic pulse 39 is stored for reference in generating the excitation signal during the acquisition of the speed of sound and the acoustic impedance. Also, the magnitude of the reflected sonic pulse 41 is stored in memory to use in determining when the excitation signal requires calibration.

Figure 6:
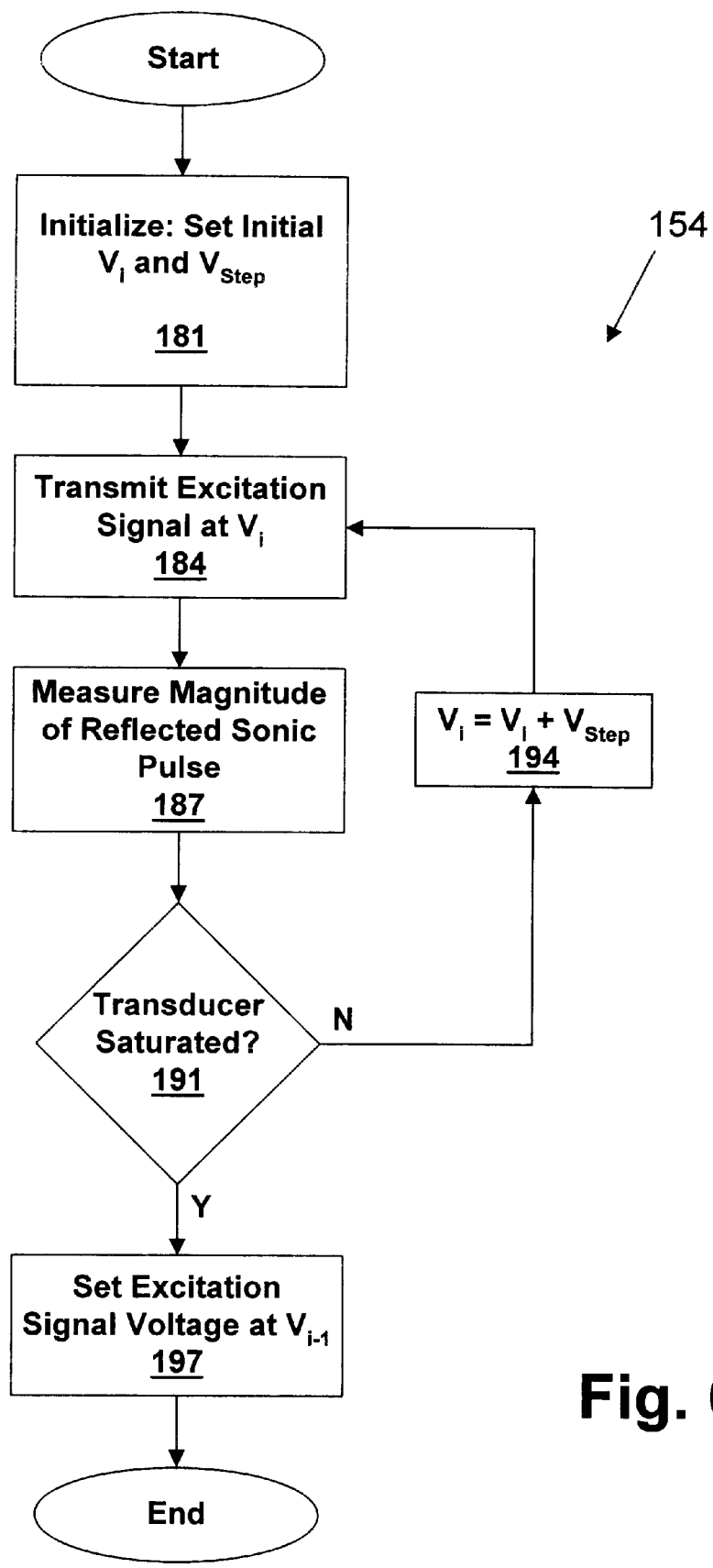
FIG. 6 is a flow chart illustrating the operating logic employed in the calibration of the magnitude of the excitation voltage of FIG. 5.

Turning next to FIG. 6, a flow chart of the operating logic performed by the subroutine in calibrating the voltage of the excitation signal in block 154 (FIG. 5) is shown. In block 181, the voltage calibration subroutine 154 is initialized where an initial predetermined value is assigned for the excitation voltage variable $V_i$, and value is assigned for a voltage step $V_{Step}$. Next, in block 184, the excitation signal is transmitted to the transducer 37 (FIG. 1) with a magnitude of $V_i$. In block 187, the magnitude of the reflected sonic pulse 41 (FIG. 1) is measured. In block 191, the magnitude of the reflected sonic pulse 41 resulting from an excitation signal of $V_i$ is compared with the magnitude at $V_{i-1}$. If the magnitude of the reflected sonic pulse 41 resulting from the excitation signal at $V_i$ is greater than $V_{i-1}$, then maximum extension of the membrane 77 (FIG. 2) of the transducer 37 has not been achieved as known in the art. In such a case, the operating logic 154 progresses to block 194 where the voltage variable $V_i$ is incremented by $V_{Step}$ and then block 184 is repeated.

If, on the other hand, the magnitude of the reflected sonic pulse 41 with an excitation signal of $V_i$ is equal to the magnitude at $V_{i-1}$, then saturation of the transducer 37 has occurred. In effect, the membrane 77 is at maximum extension and a higher voltage magnitude of the excitation frequency does not create a sonic pulse 39 (FIG. 1) of greater magnitude as is known by those skilled in the art. In this case, the operating logic progresses to block 197 where the magnitude of the voltage signal is set equal to $V_{i-1}$ which is the magnitude of the voltage of the excitation signal just before saturation of the transducer 37 which results in maximum membrane 77 extension.

Figure 7:
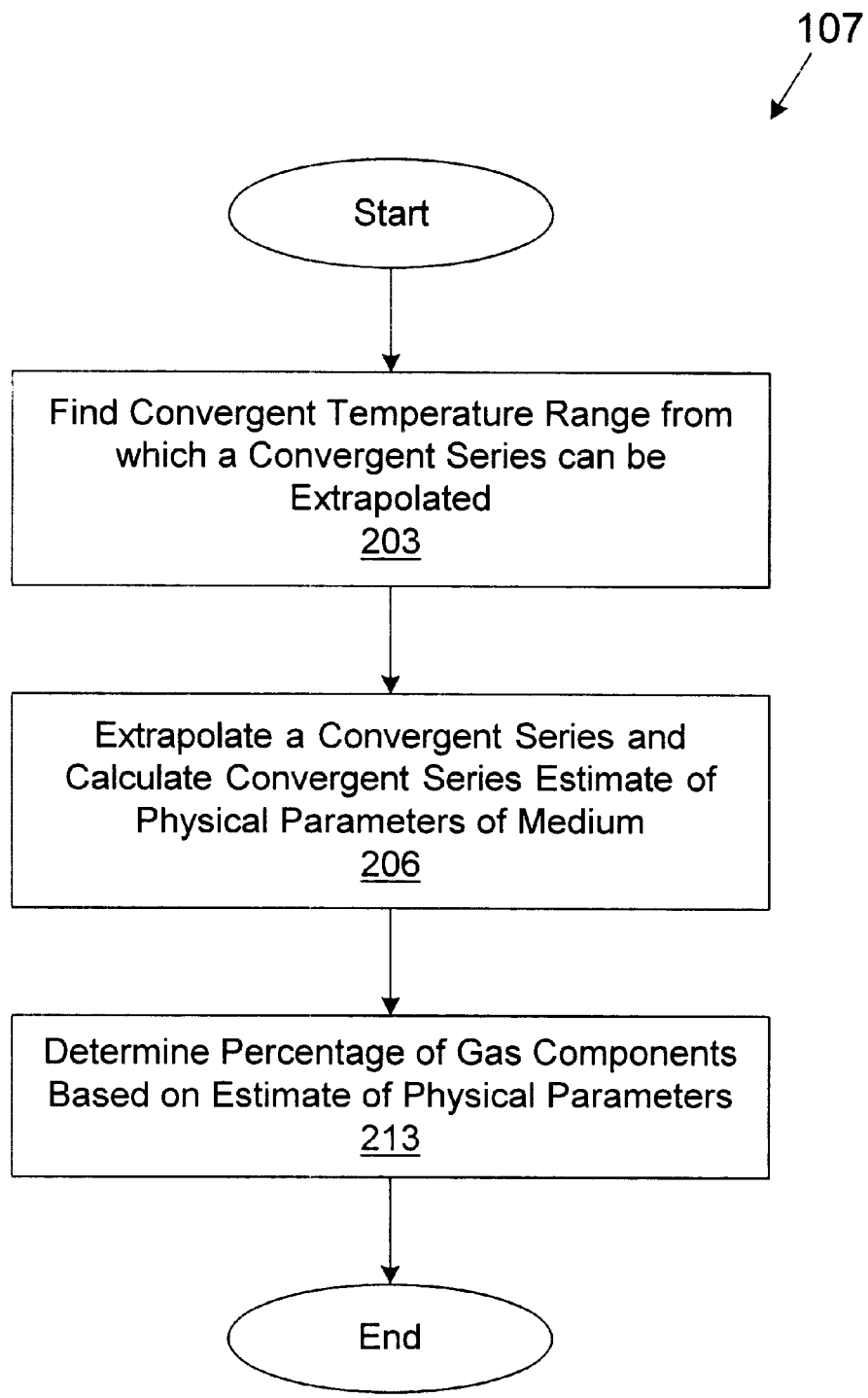
FIG. 7 is a flow chart illustrating a subroutine employed in the extrapolation of a convergence series, calculation of thermo-physical properties, and determination of the make up of the multi-component gas of FIG. 3.

Referring next to FIG. 7, shown is the gas component percentage subroutine 107 which is executed by the operating logic 61 (FIG. 3). The subroutine 107 begins with step 203 in which the temperature data stored in the computer memory 57 is examined in order to obtain or estimate a proper convergent temperature range from which a convergent temperature series may be extrapolated in order to perform a convergent series calculation as will be discussed. Specifically, the convergent temperature range comprises a predetermined range of temperature measurements, each with corresponding pressure and speed of sound measurements.

The convergent temperature range can be obtained in any one of a number of ways. For example, such temperature information may be compiled and estimated over time or over different areas in the pipe 31. For example, the temperature of the medium 34 in the pipe 31 may fluctuate over time where periodic measurements are taken, or measurements are taken at predetermined temperature values. Also, it may be possible that specific zones in the pipe 31 may have different temperatures in relation to each other due to the dynamics of fluid flow through the pipe. For example, temperatures at the sides of the pipe 31 may be different than the temperatures in the middle, or the temperature of the medium 34 as it flows through an elbow or other similar pipe structure might create zones of differing temperature. A pipe 31 may be partially exposed to different external environments which have different temperatures, thereby effecting the internal temperature of the medium 34. These temperature measurements and corresponding pressure and speed of sound measurements taken are preferably stored in the memory 57 for a predetermined period of time on a first-in-first-out basis to ensure that the convergent series estimate is relatively recent.

Once a proper convergent temperature range is obtained or estimated, then the subroutine 107 continues to block 206 in which a convergent series is extrapolated and a convergent series calculation is performed in order to estimate the physical parameters of the medium 31 as will be discussed. Thereafter, in block 213 the percentage of each gas component that makes up the gas medium 34 is determined by using state equations known by those skilled in the art. The subroutine 107 includes logic to perform these calculations.

Calculating Thermodynamic Properties

Before any discussion on the particular operating logic by which the convergent series calculations are performed, the following discourse is offered which relates to the derivation of the isobaric and isochoric equations for transforming speed of sound data into compression factor and heat capacity values from which other thermo-physical properties may be determined. Further discussion of this subject matter is found in the United States patent application entitled "Apparatus and Method for Determining Thermophysical Properties Using an Isochoric Approach" filed on Jul. 30, 1997 and afforded Ser. No. 08/903,069, the entire text of which is incorporated herein by reference.

The development begins with the definition of the thermophysical speed of sound in an unbound fluid, $$u^2 = \left(\frac{\partial P}{\partial \rho}\right)_S \qquad 1.0$$

where P is pressure, $\rho$ is molar density, and S is entropy. The cyclical relation $$\left(\frac{\partial P}{\partial \rho}\right)_S \left(\frac{\partial \rho}{\partial S}\right)_P \left(\frac{\partial S}{\partial P}\right)_\rho = -1 \qquad 1.1$$

can be substituted into equation 1.0 to give $$u^2 = \left(\frac{\partial S}{\partial \rho}\right)_P \left(\frac{\partial P}{\partial S}\right)_\rho \qquad 1.2$$

Using thermo-physical relations, equation 1.2 can be transformed into two different sets of differential equations as will be shown.

Derivation of Isochoric Speed of Sound Equations

In a first embodiment, the speed of sound data is measured in an isochoric measurement scheme. If entropy is assumed to be a function of temperature and density, the total derivative of entropy can be written as $$dS = \left(\frac{\partial S}{\partial T}\right)_\rho dT + \left(\frac{\partial S}{\partial \rho}\right)_T d\rho. \qquad 2.0$$

The partial derivatives in equation 2.0 can be defined using the definition of the isochoric heat capacity $$\left(\frac{\partial S}{\partial T}\right)_\rho = \frac{C_V}{T}, \qquad 2.1$$

and the Maxwell relation $$\left(\frac{\partial S}{\partial \rho}\right)_T = -\frac{1}{\rho^2}\left(\frac{\partial P}{\partial T}\right)_\rho. \qquad 2.2$$

Equations 2.1 and 2.2 are substituted for the partial differentials in equation 2.0, the resulting equation being $$dS = \frac{C_V}{T} dT - \frac{1}{\rho^2}\left(\frac{\partial P}{\partial T}\right)_\rho d\rho. \qquad 2.3$$

Next, equation 2.3 is divided by the partial differential of density at constant pressure. The resulting equation $$\left(\frac{\partial S}{\partial \rho}\right)_P = \frac{C_V}{T}\left(\frac{\partial T}{\partial \rho}\right)_P - \frac{1}{\rho^2}\left(\frac{\partial P}{\partial T}\right)_\rho \qquad 2.4$$

is then substituted into equation 1.2. Also, equation 2.3 is divided by the partial of pressure at constant density. The second resulting equation $$\left(\frac{\partial S}{\partial P}\right)_\rho = \frac{C_V}{T}\left(\frac{\partial T}{\partial P}\right)_\rho \qquad 2.5$$

is also substituted into equation 1.2. With these substitutions, equation 1.2 becomes $$u^2 = -\left[\frac{C_V}{T}\left(\frac{\partial T}{\partial \rho}\right)_P - \frac{1}{\rho^2}\left(\frac{\partial P}{\partial T}\right)_\rho\right]\frac{T}{C_V}\left(\frac{\partial P}{\partial T}\right)_\rho, \qquad 2.6$$

which is further simplified into $$u^2 = \left(\frac{\partial P}{\partial \rho}\right)_T + \frac{T}{\rho^2 C_V}\left(\frac{\partial P}{\partial T}\right)_\rho^2. \qquad 2.7$$

Next the partial derivative of equation 2.1 of the isochoric heat capacity with respect to molar density at constant temperature reveals $$\left(\frac{\partial C_V}{\partial \rho}\right)_T = T\frac{\partial}{\partial \rho}\left[\left(\frac{\partial S}{\partial T}\right)_\rho\right]_T. \qquad 2.8$$

Using the Maxwell relation given in equation 2.2, equation 2.8 can be expressed as $$\left(\frac{\partial C_V}{\partial \rho}\right)_T = -\frac{T}{\rho^2}\left(\frac{\partial^2 P}{\partial T^2}\right)_\rho. \qquad 2.9$$

Although equations 2.7 and 2.9 can be solved for molar density and isochoric heat capacity, it is preferable to solve these equations with the more slowly varying compression factor, Z, instead of the molar density. Thus equation 2.7 becomes $$u^2 = \frac{RT}{M}\left\{\left[Z + \rho\left(\frac{\partial Z}{\partial \rho}\right)_T\right] + \frac{R}{C_V}\left[Z + T\left(\frac{\partial Z}{\partial T}\right)_\rho\right]^2\right\}, \quad 2.10$$

and equation 2.9 becomes $$\left(\frac{\partial C_V}{\partial \rho}\right)_T = -\frac{R}{\rho}\left[2T\left(\frac{\partial Z}{\partial T}\right)_\rho + T^2\left(\frac{\partial^2 Z}{\partial T^2}\right)_\rho\right], \quad 2.11$$

where M is the molecular mass and R is the universal gas constant. Equations 2.10 and 2.11 can be rearranged to solve for $C_V$ and $$\left(\frac{\partial^2 Z}{\partial T^2}\right)_\rho,$$

resulting in $$C_V = \frac{R\left[Z + T\left(\frac{\partial Z}{\partial T}\right)_\rho\right]^2}{u^2\left(\frac{M}{RT}\right) - Z - \rho\left(\frac{\partial Z}{\partial \rho}\right)_T} \quad 2.12$$

$$\left(\frac{\partial^2 Z}{\partial T^2}\right)_\rho = -\frac{\frac{\rho}{R}\left(\frac{\partial C_V}{\partial \rho}\right)_T + 2T\left(\frac{\partial Z}{\partial T}\right)_\rho}{T^2}. \quad 2.13$$

The solution of these two equations requires initial values of Z and $$\left(\frac{\partial Z}{\partial T}\right)_\rho$$

on all isochores at the lowest temperature. Finally, the compression factor is solved for using the above derived variables using the following Taylor Series Approximations:

$$Z_1 = Z_0 + \Delta T\left(\frac{\partial Z_0}{\partial T}\right)_\rho + \frac{1}{2}\Delta T^2\left(\frac{\partial^2 Z_0}{\partial T^2}\right)_\rho, \text{ and} \quad 2.14$$

$$\left(\frac{\partial Z_1}{\partial T}\right)_\rho = \left(\frac{\partial Z_0}{\partial T}\right)_\rho + \Delta T\left(\frac{\partial^2 Z^0}{\partial T^2}\right)_\rho. \quad 2.15$$

Derivation of Isobaric Speed of Sound Equations

In a second embodiment, speed of sound data is measured in an isobaric scheme. If entropy is assumed to be a function of temperature and pressure, the total derivative of entropy can be written as $$dS = -\left(\frac{\partial S}{\partial T}\right)_P dT + \left(\frac{\partial S}{\partial P}\right)_T dP. \quad 3.0$$

The partial derivatives in equation 3.0 are defined using the definition of the isobaric heat capacity $$C_P = T\left(\frac{\partial S}{\partial T}\right)_P, \quad 3.1$$

and the Maxwell relation $$\left(\frac{\partial S}{\partial P}\right)_T = -\frac{1}{\rho^2}\left(\frac{\partial \rho}{\partial T}\right)_P. \quad 3.2$$

Equation 3.0 can then be rewritten as $$dS = \frac{C_P}{T}dT + \frac{1}{\rho^2}\left(\frac{\partial \rho}{\partial T}\right)_P dP. \quad 3.3$$

Equation 3.3 is then divided by the partial derivative of density at constant pressure. The resulting equation $$\left(\frac{\partial S}{\partial \rho}\right)_P = \frac{C_P}{T}\left(\frac{\partial T}{\partial \rho}\right)_P. \quad 3.4$$

is substituted into equation 1.2. Also, equation 3.3 is divided by the partial derivative of pressure at constant density. The resulting equation $$\left(\frac{\partial S}{\partial P}\right)_\rho = \frac{C_P}{T}\left(\frac{\partial T}{\partial P}\right)_\rho - \frac{1}{\rho^2}\left(\frac{\partial \rho}{\partial T}\right)_P. \quad 3.5$$

is also substituted into equation 1.2. With these substitutions, equation 1.2 becomes $$u^2 = -\frac{C_P}{T}\left(\frac{\partial T}{\partial \rho}\right)_P\left[\frac{C_P}{T}\left(\frac{\partial T}{\partial P}\right)_\rho + \frac{1}{\rho^2}\left(\frac{\partial \rho}{\partial T}\right)_P\right]^{-1} \quad 3.6$$

which can be simplified into $$u^2 = \left[\left(\frac{\partial \rho}{\partial P}\right)_T + \frac{T}{\rho^2 C_P}\left(\frac{\partial \rho}{\partial T}\right)_P^2\right]^{-1}. \quad 3.7$$

Next, the partial derivative of the isobaric heat capacity of equation 3.7 with respect to pressure at constant temperature is taken, resulting in $$\left(\frac{\partial C_P}{\partial P}\right)_T = T\left(\frac{\partial}{\partial P}\right)\left[\left(\frac{\partial S}{\partial T}\right)_P\right]_T. \quad 3.8$$

Using the Maxwell relation given in equation 3.2, equation 3.8 becomes $$\left(\frac{\partial C_P}{\partial P}\right)_T = -T\left(\frac{\partial^2 \rho^{-1}}{\partial T^2}\right)_P \quad 3.9$$

Although equations 3.7 and 3.9 can be solved for molar density and isobaric heat capacity, it is preferable to solve these equations with the more slowly varying compression factor, Z, instead of the molar density. Thus equation 2.7 becomes $$u^2 = \frac{M}{RTZ^2}\left[Z - P\left(\frac{\partial Z}{\partial P}\right)_T\right] - \left(\frac{1}{C_P TZ^2}\right)\left[Z + T\left(\frac{\partial Z}{\partial T}\right)_P\right]^2 \quad 3.10$$

and equation 2.9 becomes $$\left(\frac{\partial C_P}{\partial P}\right)_T = -\frac{R}{P}\left[2T\left(\frac{\partial Z}{\partial T}\right)_P + T^2\left(\frac{\partial^2 Z}{\partial T^2}\right)_P\right]. \qquad 3.11$$

where M is the molecular mass, and R is the universal gas constant. Equations 3.10 and 3.11 are then rearranged to solve for $C_P$ and $$\left(\frac{\partial^2 Z}{\partial T^2}\right)_P,$$

resulting in $$C_P = \frac{R\left[Z + T\left(\frac{\partial Z}{\partial T}\right)_P\right]^2}{u^{-2}\left(\frac{RTZ^2}{M}\right) - Z + P\left(\frac{\partial Z}{\partial P}\right)_T}, \text{ and} \qquad 3.12$$

$$\left(\frac{\partial^2 Z}{\partial T^2}\right)_P = -\frac{\frac{P}{R}\left(\frac{\partial C_P}{\partial P}\right)_T + 2T\left(\frac{\partial Z}{\partial T}\right)_P}{T^2}. \qquad 3.13$$

The solution of equations 3.12 and 3.13 require initial values for Z and $$\left(\frac{\partial Z}{\partial T}\right)_P$$

on all isobars at the lowest temperature. Finally, the compression factor is solved for using the above derived variables using the following Taylor Series Approximations:

$$Z = Z_0 + \Delta T\left(\frac{\partial Z_0}{\partial T}\right)_P + \frac{1}{2}\Delta T^2\left(\frac{\partial^2 Z_0}{\partial T^2}\right)_P, \text{ and} \qquad 3.14$$

$$\left(\frac{\partial Z}{\partial T}\right)_P = \left(\frac{\partial Z_0}{\partial T}\right)_P + \Delta T\left(\frac{\partial^2 Z_0}{\partial T^2}\right)_P. \qquad 3.15$$

Convergence Using Isochoric Equations

In the following discussion, the first embodiment is described in which the formulas derived above relating to the isochoric speed of sound are employed to ascertain accurate thermo-physical properties of a volume of a particular multi-component medium.

To begin, a temperature range is specified over which measurements of the speed of sound and the pressure of the particular volume of multi-component medium will be taken. Also, a temperature step $\Delta T$ is chosen at which to take these measurement across the range specified. Note, however, that the temperature step $\Delta T$ need not be uniform across the temperature range. Uniformity may be achieved by interpolation techniques as known to those skilled in the art.

Next, the temperature of the medium is brought to either the low end, $T_{LOW}$, or the high end, $T_{HIGH}$, of the temperature range to begin taking measurements of physical parameters. The deciding factor as to whether to us $T_{LOW}$ or $T_{HIGH}$ as the beginning point is that no particular component of the medium be at or near the liquid stage. If no component is at or near the liquid stage at $T_{LOW}$, then this temperature may be used as the starting point. This is to ensure that the multi-component medium is a uniform mixture.

In the case where $T_{LOW}$ is chosen as to start, the temperature of the medium is then raised in steps by $\Delta T$. In the case where $T_{HIGH}$ is chosen as to start, the temperature of the medium is lowered in steps by $\Delta T$. In either case, at each step the pressure P and speed of sound u of the medium are measured. This cycle of raising or lowering the temperature in steps of $\Delta T$ and measuring the pressure and speed of sound at each step is continued until measurements have been taken across the entire specified temperature range. The temperatures, pressures and speed of sound for each temperature increment are stored in memory for further evaluation. During the entire process, the density $\rho$ is kept nearly constant. There may be slight fluctuation of the density $\rho$ due to deformity of any vessel in which the medium is held caused by changing pressure P. However, the substance of the medium will remain the same.

After the values of the temperature, pressure, and speed of sound have been determined for each interval across the specified range, an iterative process based on these measurements is undertaken in which the thermo-physical properties of the multi-component medium are ascertained. According to the first embodiment, new and more accurate values for the compressibility Z, density $\rho$ and $$\left(\frac{\partial Z}{\partial T}\right)$$

are calculated for each $\Delta T$ starting at $T_{LOW}$ using the Z, $\rho$ and $$\left(\frac{\partial Z}{\partial T}\right)$$

from the previous calculation as initial values, thereby converging on more precise values for these properties across the specified temperature range. For the first calculation at the first $\Delta T$, an estimate of the Z, $\rho$ and $$\left(\frac{\partial Z}{\partial T}\right)$$

are used as initial values.

A single iteration of the process comprises performing the calculations for all $\Delta T$'s across the specified temperature range. The density $\rho$ that results from each iteration is used as the initial density $\rho$ in the subsequent iteration. Based on the new density that emerges, the initial estimates of Z and $$\left(\frac{\partial Z}{\partial T}\right)$$

are updated. With each iteration performed, the density will converge to the actual value of the density of the multi-component medium. Likewise, the specific heat $C_V$ and compressibility Z calculated in each iteration will converge to accurate values as well. In the preferred form of the first embodiment, the iterations are performed on a computing system which will allow many iterations to be performed in a small period of time.

To describe in detail the calculations performed for each $\Delta T$, first, initial values for the compressibility Z, density $\rho$, and $$\left(\frac{\partial Z}{\partial T}\right)$$

of the medium are determined. These values may be estimated in one of several ways, including the use of any equation of state or other methods known to those skilled in the art. In particular, detailed knowledge of the gas composition is not required to obtain the values needed to initiate the calculations. A reasonable estimate of the gas composition from which the initial compressibility Z, density ρ, and $$\left(\frac{\partial Z}{\partial T}\right)$$

can be determined using an equation of state is recommended. In the first embodiment, the equation of state disclosed in the American Gas Association Report No. 8, version 1.2 dated July, 1994 is used due to its relatively greater accuracy as known by those skilled in the art. A reasonable estimate for the compositions of typical natural gasses could be, for example, pure methane or any of the appropriate natural gas compositions in American Gas Association Report No. 8. Also, these estimates can be made on the basis of other measurements as known to those skilled in the art or based on experience with the particular type of fluid, the compositions of which are generally known over a period of time.

Once values for each of these variables are estimated, the numerical derivative of the compressibility Z with respect to density ρ at constant temperature, denoted as $$\left(\frac{\partial Z}{\partial T}\right)_T$$

is determined. The numerical derivative may be expressed as $$\left(\frac{\partial Z}{\partial \rho}\right)_T = \frac{Z(\rho + \Delta\rho, T) - Z(\rho - \Delta\rho, T)}{2\Delta\rho}.$$

Generally, the numerical derivative $$\left(\frac{\partial Z}{\partial \rho}\right)_T$$

may be calculated from measurements at an isochore both above and below the current isochore as known to those skilled in the art.

Next, the isochoric heat capacity $C_V$ is found using previously derived equation 2.12 which, once again, is expressed as $$C_V = \frac{R\left[Z + T\left(\frac{\partial Z}{\partial T}\right)_\rho\right]^2}{u^2\left(\frac{M}{RT}\right) - Z - \rho\left(\frac{\partial Z}{\partial \rho}\right)_T} \quad 2.12$$

where M is the molecular mass and R is the universal gas constant.

Once the isochoric heat capacity $C_V$ is determined, the numerical derivative of the heat capacity $C_V$ with respect to the density ρ at constant temperature, denoted as $$\left(\frac{\partial C_V}{\partial \rho}\right)_T,$$

is determined. The numerical derivative $$\left(\frac{\partial C_V}{\partial \rho}\right)_T$$

may be expressed as $$\left(\frac{\partial C_V}{\partial \rho}\right)_T = \frac{C_V(\rho + \Delta\rho, T) - C_V(\rho - \Delta\rho, T)}{2\Delta\rho}.$$

Generally, the numerical derivative may be calculated from measurements at an isochore both above and below the current isochore as known to those skilled in the art.

Once the numerical derivative $$\left(\frac{\partial C_V}{\partial \rho}\right)_T$$

is known, then a solution may be found for $$\left(\frac{\partial^2 Z}{\partial T^2}\right)_\rho$$

using equation 2.13 which, once again is expressed as $$\left(\frac{\partial^2 Z}{\partial T^2}\right)_\rho = -\frac{\frac{\rho}{R}\left(\frac{\partial C_V}{\partial \rho}\right)_T + 2T\left(\frac{\partial Z}{\partial T}\right)_\rho}{T^2},$$

where R is the universal gas constant.

Finally, new values for the compressibility Z and the partial derivative $$\left(\frac{\partial Z}{\partial T}\right)_\rho$$

are found with the variables determined above using the Taylor series approximations of equations 2.14 and 2.15 denoted as $$Z_{NEW} = Z + \Delta T\left(\frac{\partial Z}{\partial T}\right)_\rho + \frac{1}{2}\Delta T^2\left(\frac{\partial^2 Z}{\partial T^2}\right)_\rho, \text{ and} \quad 2.14$$

$$\left[\left(\frac{\partial Z}{\partial T}\right)_\rho\right]_{NEW} = \left(\frac{\partial Z}{\partial T}\right)_\rho + \Delta T\left(\frac{\partial^2 Z}{\partial T^2}\right)_\rho. \quad 2.15$$

The new values for the compressibility Z and the partial derivative $$\left(\frac{\partial Z}{\partial T}\right)_\rho$$

are more accurate than the originally estimated initial values. A new, more accurate value for the density ρ may then be calculated from the compressibility Z as known by those skilled in the art. The foregoing calculations are repeated at the next ΔT, using the new measurements for the temperature T, the speed of sound u, and pressure P and the new values for the compressibility Z, the partial derivative $$\left(\frac{\partial Z}{\partial T}\right)_\rho,$$

and the density ρ previously calculated. This process is repeated for each ΔT, causing the heat capacity $C_V$, the compressibility Z, and the partial derivative $$\left(\frac{\partial Z}{\partial T}\right)_\rho$$

to converge to their actual values. Also, the density ρ which is calculated from these parameters in turn becomes more accurate.

The calculation of the compressibility Z, partial derivative $$\left(\frac{\partial Z}{\partial T}\right)_\rho,$$

and density ρ across a single specified temperature range makes a single iteration. The value for the density ρ that results from a single iteration may be used as the initial value (previously estimated) of the density ρ for a second iteration which is performed based on the same measured values for the temperature T, pressure P, and speed of sound u at the same temperature intervals of ΔT. The initial values for the compressibility Z and the partial derivative $$\left(\frac{\partial Z}{\partial T}\right)$$

may be estimated again based on the new value of the density ρ. In this fashion, several iterations are possible, each of which will cause the density ρ, the compressibility Z and the partial derivative $$\left(\frac{\partial Z}{\partial T}\right)$$

to converge on their actual values. The total number of iterations that may be performed are those necessary to achieve the desired accuracy of the calculated parameters.

After accurate values for the density ρ, heat capacity $C_V$, the compressibility Z, and the partial derivative $$\left(\frac{\partial Z}{\partial T}\right)_\rho$$

have been determined, other thermo-physical properties are then calculated from these properties using various thermo-physical equations as known by those skilled in the art. These properties would include the compressibility factor, the heat capacity, entropy, enthalpy, free energy, internal energy and other related properties.

Extrapolation of Conversion Series From Real Time Measurements

According to the above discussion, isochoric convergence for values of density ρ, the compressibility Z and the partial derivative $$\left(\frac{\partial Z}{\partial T}\right)$$

requires a series of pressure and speed of sound measurements over a specific range of temperature values, defined herein as a convergence series. In the present invention, the convergence series is extrapolated from the measurements of the temperature, pressure, speed of sound, and acoustic impedance acquired according to the operating logic of block 104 (FIG. 3).

Figure 8:
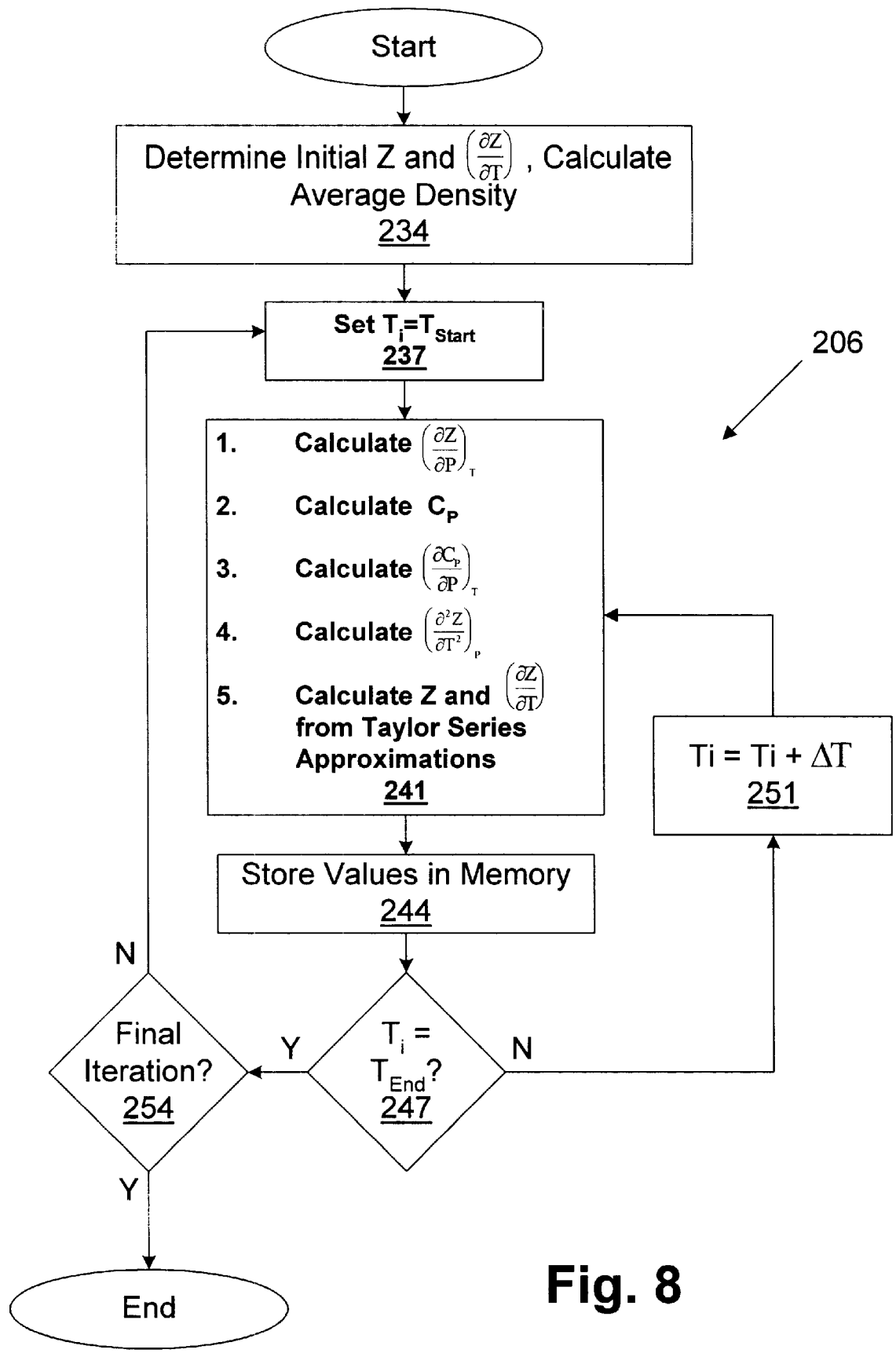
FIG. 8 is a flow chart of a subroutine of FIG. 7 that is executed to calculate the thermo-physical properties.

Turning then to FIG. 8, a flow chart of the operating logic by which the convergence series is extrapolated and the isochoric convergence is performed of block 111 (FIG. 3). Once an acceptable convergent temperature range is determined in block 206 (FIG. 7), the values are manipulated as according to the following discussion. In block 234, a value is determined for ΔT where $\Delta T = abs(T_{Start} - T_{End})/X_i$, where $T_{Start}$ and $T_{End}$ are the highest and lowest temperature measurements in the convergent temperature range. Essentially, this creates uniform ΔT's with which to perform the calculation. The value of $X_i$ determines how many different temperature steps there are to be in the calculation. Generally, the choice of values for $X_i$ effects the extent of the convergence. If $X_i$ is relatively high, then the temperature step ΔT may be small thereby lowering the level of convergence of the values for density ρ, the compressibility Z and the partial derivative $$\left(\frac{\partial Z}{\partial T}\right).$$

If $X_i$ is too low, then there may not be enough calculations within a single iteration to cause effective convergence as well. Thus the value for $X_i$ is chosen with these concepts in mind.

With the value for ΔT known, next corresponding values for the pressure and speed of sound are extrapolated from the values of the convergent temperature range stored corresponding to the various temperature measurements taken. The extrapolation of these values is an expedient known to those skilled in the art and is not discussed in detail.

Also in block 234, initial values for Z and $$\left(\frac{\partial Z}{\partial T}\right)$$

are estimated along with an estimate of the density ρ. Recall that the acoustic impedance was proportional to magnitude of the voltage of the excitation signal at maximum power transfer. This proportionality may be determined by using an experimental method where the transducer is placed in a medium of known density, which is an expedient known in the art and not discussed in detail. It is also observed the density of the medium 34 (FIG. 1) is related to the speed of sound and the acoustic impedance according to the equation $$\rho = \frac{\beta}{v^2},$$

where β is the acoustic impedance of the medium 34, v is the speed of sound, and ρ is the density of the medium 34. The acoustic impedance β may be expressed in terms of $N/m^2$, the speed of sound is in m/s, and the density is expressed in terms of $kg/m^3$. As known to one skilled in the art, the above units are in the metric system.

For each measurement of the acoustic impedance and the speed of sound in the convergent series from $T_{Start}$ to $T_{End}$, a corresponding value for the density ρ may be calculated. An estimate for the density may then be determined by averaging the densities calculated over the convergence series.

The operating logic then progresses to block 237 where the temperature variable $T_i$ is set equal to $T_{Start}$ which is the beginning temperature value of the convergence series. Next, in block 241, the isochoric calculations are performed using the equations previously discussed, resulting in new values for the density ρ, the compressibility Z and the partial derivative $$\left(\frac{\partial Z}{\partial T}\right).$$

In block 244, these new values are stored in memory.

Moving to block 247, it is determined whether $T_i$ is equal to $T_{End}$ which is the last temperature in the convergence series. If $T_{End}$ has not been reached, then the operating logic progresses to block 251 where the temperature variable $T_i$ is incremented or decremented by ΔT, depending on whether the convergence series calculations are performed using increasing or decreasing temperature values. From block 251, the operating logic progresses to block 241 where the calculations are repeated.

If, on the other hand, the temperature variable $T_i$ has been reached, then the operating logic progresses to block 254 where it is determined whether further iterations are to be performed across the convergence series. If so, then the logic progresses to block 237 where the process is repeated using the last calculated values for the density ρ, the compressibility Z and the partial derivative $$\left(\frac{\partial Z}{\partial T}\right).$$

The number of iterations to be performed is a function the desired degree of accuracy of the variables. If greater accuracy is desired, then a greater number of iterations can be performed or vice versa. The use of a microprocessor based computer system allows many iterations to be performed in a very short period of time, making greater accuracy feasible. It may be configured that the iterations are performed indefinitely, being interrupted only when a new convergence series is introduced when an acceptable temperature gradient is detected. However, if no further iterations are to be performed, then the operating logic ceases performing the subroutine of block 111 (FIG. 3).

As stated previously, after accurate values for the density ρ, heat capacity $C_V$, the compressibility Z, and the partial derivative $$\left(\frac{\partial Z}{\partial T}\right)_\rho$$

have been determined, other thermo-physical properties are then calculated from these properties using various thermo-physical equations as known by those skilled in the art. These properties would include the compressibility factor, the heat capacity, entropy, enthalpy, free energy, internal energy and other related properties.

Many variations and modifications may be made to the preferred embodiment of the invention without departing substantially from the spirit and principles of the invention. All such modifications and variations are intended to be included herein within the scope of the present invention, as defined by the following claims.

The invention claimed is:

1. A system for determining the thermodynamic properties of a gas medium, comprising:

a transducer disposed in the gas medium to emit a sound pulse based on an excitation signal having a voltage V and frequency f into the gas medium and detecting the return pulse therefrom;

a temperature sensor disposed in the gas medium to measure the temperature of the gas medium;

a pressure sensor disposed in the gas medium to measure the pressure of the gas medium;

means for acquiring and storing measurements of the speed of sound in the gas medium, the acoustic impedance of the gas medium, the pressure and temperature of the gas medium;

means for determining the thermodynamic properties of the gas medium based on the stored measurements;

means for detecting the existence of a temperature gradient of a predetermined range among the stored measurements; and means for determining the percentage of a plurality of gas components making up the gas medium.

2. The system of claim 1, further comprising means for calibrating the frequency and voltage of the excitation signal to achieve maximum power transfer into the medium.

3. The system of claim 2, wherein the means for acquiring and storing measurements of the acoustic impedance of the gas medium further comprises calculating the acoustic impedance based on the excitation signal, wherein the acoustic impedance is proportional to the calibrated voltage of the excitation signal at maximum power transfer.

4. The system of claim 3, wherein the means for determining the thermodynamic properties of the gas medium further comprises the calculation of the density of the gas medium based upon the acoustic impedance and the speed of sound through the gas medium, where $$\rho = \frac{\beta}{v^2},$$

where ρ is the density, β is the acoustic impedance, and v is the speed of sound through the gas medium.

5. A system for determining the thermodynamic properties of a gas medium comprising:

a transducer disposed in the gas medium to emit a sound pulse based on an excitation signal having a voltage V and frequency f into the gas medium and detecting a return pulse therefrom, the transducer being in electrical communication with a transducer interface, the transducer interface being electrically coupled to a data bus;

a temperature sensor disposed in the gas medium to measure the temperature of the gas medium, the temperature sensor being in electrical communication with a temperature probe interface, the temperature probe interface being electrically coupled to the data bus;

a pressure sensor disposed in the gas medium to measure the pressure of the gas medium, the pressure sensor being in electrical communication with a pressure transducer interface, the pressure transducer interface being electrically coupled to the data bus;

a microprocessor electrically coupled to the data bus;

a memory electrically coupled to the data bus; and operating logic stored in the memory, the operating logic directing the acquisition and storage in memory of measurements of the speed of sound and the acoustic impedance of the gas medium using the transducer, measurements of the pressure of the gas medium using the temperature sensor and detection of the existence of a temperature gradient of a predetermined range among stored temperature measurements, the operating logic further calculating the thermodynamic properties of the gas medium based on the stored measurements.

6. The system of claim 5, wherein the operating logic further comprises the calibration of the frequency and voltage of the excitation signal to achieve maximum power transfer into the gas medium.

7. The system of claim 6, wherein the operating logic further comprises the calculation of the acoustic impedance based on the excitation signal, wherein the acoustic impedance is proportional to the calibrated voltage of the excitation signal at maximum power transfer.

8. The system of claim 7, wherein the operating logic further comprises the calculation of the density of the gas medium based upon the acoustic impedance and the speed of sound though the gas medium, where $$\rho = \frac{\beta}{v^2},$$

where $\rho$ is the density, $\beta$ is the acoustic impedance, and $v$ is the speed of sound through the gas medium.

9. A method for determining the thermodynamic properties of a gas medium, comprising the steps of:

establishing and applying an excitation signal having a voltage V and frequency f to an acoustic transducer;

measuring the speed of sound through the gas medium;

measuring the acoustic impedance of the gas medium;

measuring the pressure of the gas medium;

measuring the temperature of the gas medium;

storing the measurements of the speed of sound, acoustic impedance, pressure, and temperature;

calculating the thermodynamic properties of the gas medium based on the stored measurements;

detecting the existence of a temperature gradient of a predetermined range among stored temperature measurements; and means for determining the percentage of a plurality of gas components making up the gas medium.

10. The method of claim 9, further comprising the step of calibrating the frequency and voltage of the excitation signal to achieve maximum power transfer into the gas medium.

11. The method of claim 10, further comprising the step of calculating the acoustic impedance based on the excitation signal, wherein the acoustic impedance is proportional to the calibrated voltage of the excitation signal at maximum power transfer.

12. The method of claim 11, further comprising the step of calculating the density of the gas medium based upon the acoustic impedance and the speed of sound through the gas medium, where $$\rho = \frac{\beta}{v^2},$$

and where $\rho$ is the density, $\beta$ is the acoustic impedance, and $v$ is the speed of sound through the gas medium.

* * * * *